United States Patent
Knierim et al.

(10) Patent No.: US 10,145,822 B2
(45) Date of Patent: Dec. 4, 2018

(54) TRI-MODE PROBE WITH AUTOMATIC SKEW ADJUSTMENT

(71) Applicant: Tektronix, Inc., Beaverton, OR (US)

(72) Inventors: Daniel G. Knierim, Beaverton, OR (US); Christopher R. Muggli, Hillsboro, OR (US); Martin Rockwell, Sherwood, OR (US); Ira G. Pollock, Hillsboro, OR (US)

(73) Assignee: Tektronix, Inc., Beaverton, OR (US)

( * ) Notice: Subject to any disclaimer, the term of this patent is extended or adjusted under 35 U.S.C. 154(b) by 0 days.

(21) Appl. No.: 14/745,757

(22) Filed: Jun. 22, 2015

(65) Prior Publication Data

US 2016/0033455 A1 Feb. 4, 2016

Related U.S. Application Data

(60) Provisional application No. 62/030,476, filed on Jul. 29, 2014.

(51) Int. Cl.
| | |
|---|---|
| *G01N 29/30* | (2006.01) |
| *G01N 29/24* | (2006.01) |
| *G01R 1/067* | (2006.01) |
| *G01R 31/317* | (2006.01) |

(52) U.S. Cl.
CPC ............. *G01N 29/30* (2013.01); *G01N 29/24* (2013.01); *G01R 1/06766* (2013.01); *G01R 1/06772* (2013.01); *G01R 31/31706* (2013.01)

(58) Field of Classification Search
CPC ................................ G01N 29/24; G01N 29/30
USPC ........................................................ 73/1.82
See application file for complete search history.

(56) References Cited

U.S. PATENT DOCUMENTS

| | | | | |
|---|---|---|---|---|
| 7,893,746 B1* | 2/2011 | Zheng | ............... | H03H 11/26 |
| | | | | 327/261 |
| 2005/0047538 A1* | 3/2005 | Jaussi | ............... | H03L 7/0814 |
| | | | | 375/355 |
| 2007/0273438 A1* | 11/2007 | Hickman | ........... | H03F 3/211 |
| | | | | 330/69 |
| 2009/0055694 A1* | 2/2009 | Ramesh | ........... | G01R 31/3171 |
| | | | | 714/700 |

(Continued)

OTHER PUBLICATIONS

Van Den Bossche Alex et al., "Two channel high voltage differential probe for power electronics applications", 2013 15th European Conference on Power Electronics and Applications (EPE), Sep. 2, 2013, pp. 1-6.

(Continued)

*Primary Examiner* — Son Le
*Assistant Examiner* — Tarun Sinha
(74) *Attorney, Agent, or Firm* — Miller Nash Graham & Dunn; Andrew J. Harrington

(57) ABSTRACT

A probe, including a first input configured to receive a first input signal, a second input configured to receive a second input signal, a first cable connected to the first input, a second cable connected to the second input, an electronically adjustable delay connected to the first cable, the electronically adjustable delay configured to delay the first input signal to remove a skew between the first input signal and the second input signal, and an amplifier configured to receive the first input signal from the electronically adjustable delay and a second input signal.

14 Claims, 3 Drawing Sheets

(56) References Cited

U.S. PATENT DOCUMENTS

| | | | |
|---|---|---|---|
| 2009/0189623 A1* | 7/2009 | Campbell | G01R 1/06772 324/756.03 |
| 2012/0126869 A1* | 5/2012 | Payne | H03L 7/0812 327/161 |
| 2013/0207643 A1 | 8/2013 | Peschke et al. | |
| 2014/0133529 A1 | 5/2014 | Ding et al. | |

OTHER PUBLICATIONS

European Search Report, dated Feb. 9, 2016, 7 Pages, EP Application No. 15178827.0, European Patent Office, Munich, Germany.

* cited by examiner

TRI-MODE PROBE WITH AUTOMATIC SKEW ADJUSTMENT

BENEFIT

This application claims the benefit of U.S. Provisional Application No. 62/030,476 filed Jul. 29, 2014 titled TRI-MODE PROBE WITH AUTOMATIC SKEW ADJUSTMENT, which is incorporated herein by reference in its entirety.

TECHNICAL FIELD

This disclosure relates to a probe with an electronically adjustable delay in at least one probe input path, and methods for automatically adjusting the electronically adjustable delay to minimize skew and mode conversion in a differential signal.

BACKGROUND

Differential input probes are commonly used to acquire a nominally differential signal, such as on a high-speed serial data bus, from a device under test (DUT) using a single test and measurement instrument channel. TriMode™ input probes have the additional capability of acquiring the common-mode signal, or either side of the differential pair signal as a single-ended signal.

An ideal differential signal includes two complementary signals sent on two separate wires. Any skew, or difference in delay, between the two sides of wiring in a DUT to the test and measurement instrument and/or within the test and measurement instrument itself causes mode conversion of the differential signal. Mode conversion is when a portion of the differential signal appears as the common-mode signal, or vice versa. Mode conversion due to skew grows progressively worse at higher frequencies. For instance, just one picosecond (ps) of skew at 25 GHz will lead to over 15% of the common-mode voltage appearing as a differential signal.

One approach to minimizing errors due to the skew-related mode conversion is to provide mechanically variable delays, e.g., trombones, in one or both probe inputs, and mechanically adjusting the mechanically variable delays to match in delay. In some cases, the adjustment may be done at probe manufacture to compensate for the mismatch in the probe cable. However, this does not help with the skew in the user's wiring from the DUT to the probe. Alternatively, the adjustment may be user-accessible, but would still be inconvenient for a user to adjust. Trombones also add to the cost of the probe and may lead to reliability issues.

Another approach to minimize the errors due to skew-related mode conversion is to use two test and measurement instrument channels to separately acquire each side of the differential pair signal. Digital signal processing is used to adjust the timing of a first channel's waveform to match the timing of a second channel's waveform. Then, the two waveforms are subtracted to find the differential signal. This method provides a form of tri-mode functionality, in that the common-mode or either single-ended signal is available depending on the math function used. However, this method is quite costly due to the need to use two channels in place of one.

Embodiments of the disclosed technology address these and other limitations in the prior art.

SUMMARY

What is needed is the ability to adjust the delays in a probe to remove the skew between the two sides of the differential signal, due to differences in wiring, to eliminate or minimize mode conversion in the differential signal.

Certain embodiments of the disclosed technology include a probe, including a first input configured to receive a first input signal, a second input configured to receive a second input signal, a first cable connected to the first input, a second cable connected to the second input, an electronically adjustable delay connected to the first cable, the electronically adjustable delay configured to delay the first input signal to remove a skew between the first input signal and the second input signal, and an amplifier configured to receive the first input signal from the electronically adjustable delay and a second input signal.

Certain other embodiments of the disclosed technology include a method for correcting skew between a first input signal and a second input signal, the method including receiving the first input signal; receiving the second input signal; determining an amount of skew between the first input signal and the second input signal; and adjusting a delay of at least one electronically variable adjustable delay to remove the skew between the first input signal and the second input signal.

DETAILED DESCRIPTION

Figure 1:
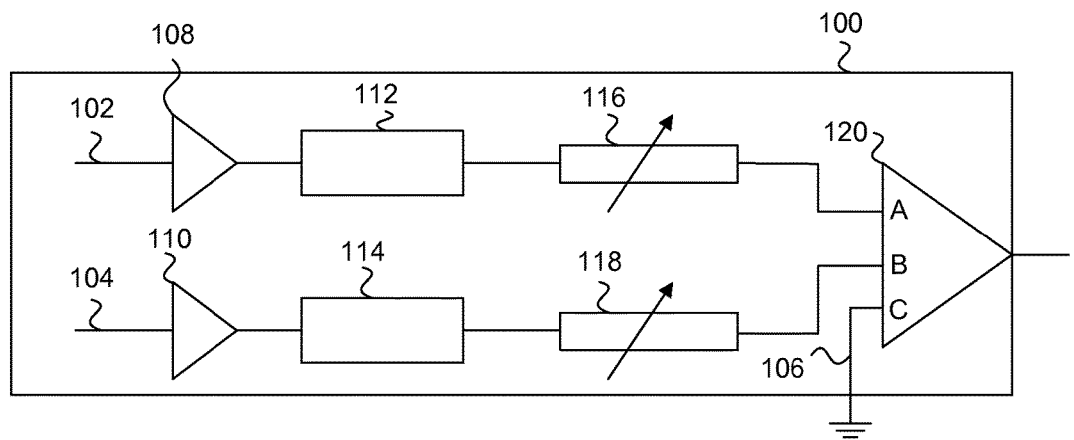
FIG. 1 illustrates a probe with an electronically adjustable delay according to some embodiments of the invention.

In the drawings, which are not necessarily to scale, like or corresponding elements of the disclosed systems and methods are denoted by the same reference numerals.

The disclosed technology relates to a probe with an electronically adjustable delay. Preferably, the probe has an electronically adjustable delay in each input path.

However, as disclosed in more detail below, some embodiments include an electronically adjustable delay in one input path while the other input has a fixed delay. The probe may be a TriMode™ probe 100 as shown in FIG. 1 that uses a single channel of a test and measurement instrument.

In some embodiments, the TriMode™ probe 100 includes three inputs 102, 104, and 106. The first input 102 receives a first signal from a device under test, the second input 104 receives a second signal from a device under test and the third input 106 is connected to ground. The TriMode™ probe 100 also includes buffers 108 and 110, cables 112 and 114, adjustable variable delays 116 and 118, and a tri-mode amplifier 120. The adjustable variable delays 116 and 118 may be separate from or integrated on the same integrated chip with the tri-mode amplifier 120.

Figure 2:
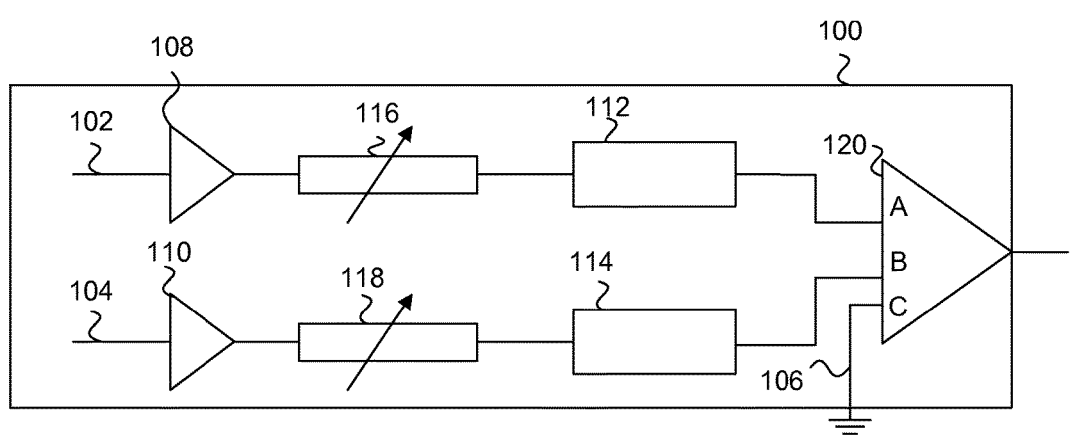
FIG. 2 illustrates another probe with an electronically adjustable delay according to some embodiments of the invention.
Figure 3:
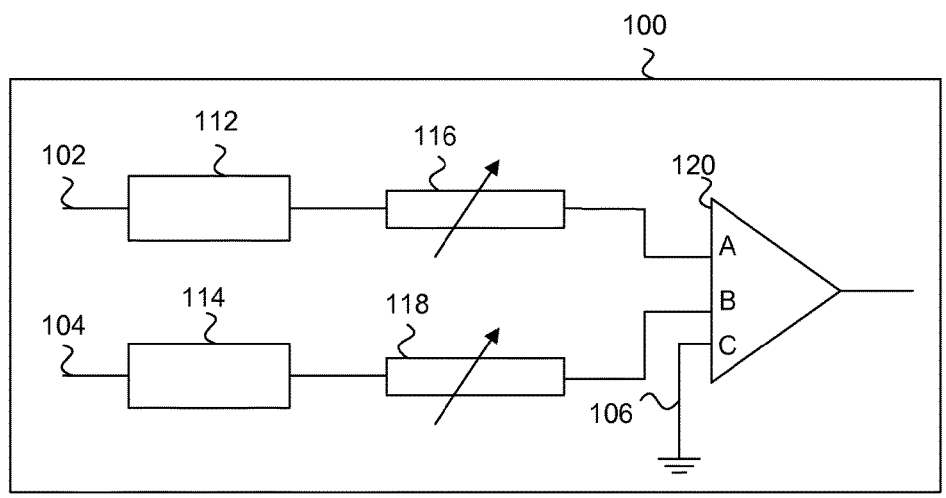
FIG. 3 illustrates another probe with an electronically adjustable delay according to some embodiments of the invention.

However, the disclosed technology is not limited to the embodiment shown in FIG. 1. For example, as seen in FIG. 2, the adjustable variable delays 116 and 118 may be placed before the cables 112 and 114, and integrated with the buffers 108 and 110. In other embodiments, as seen in FIG. 3, the buffers 108 and 110 can be eliminated if the probe is implemented for a 50Ω input use case.

Figure 4:
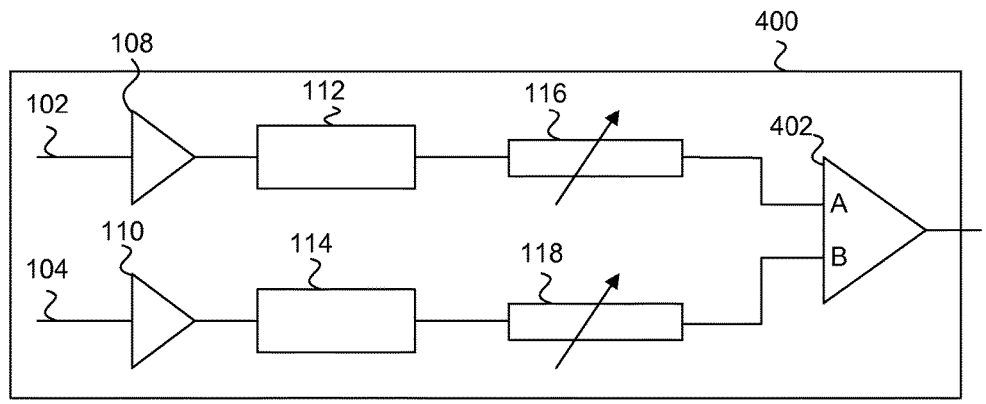
FIG. 4 illustrates another probe with an electronically adjustable delay according to some embodiments of the invention.

Although a TriMode™ probe has been discussed with respect to FIGS. 1-3, a differential probe may also be used with the disclosed technology, as will be discussed in more detail below and shown in FIG. 4. The differential probe 400 contains only two inputs 102 and 104, rather than the three inputs seen in FIGS. 1-3. The differential probe 400 also includes a differential amplifier 402, rather than a tri-mode amplifier 120.

A number of different types of broadband DC-coupled electronically adjustable variable delays 116 and 118 may be used. The electronically variable adjustable delays 116 and 118 may be chosen based on performance requirements and cost factors. For example, an electronically variable adjustable delay may be chosen based on the ability to integrate the electronically variable adjustable delay with either the buffers 108 and 110, or the tri-mode amplifier 120/differential amplifier 402.

Examples of electronically adjustable variable delays 116 and 118 that may be used are varactor tuned lumped-element delay lines, MEMS-switched delay segments, or switched active delay elements. Another example of an electronically variable delay is described in U.S. application Ser. No. 14/745,711, titled ELECTRONICALLY VARIABLE ANALOG DELAY LINE, filed Jun. 22, 2015, and incorporated herein by reference in its entirety. However, the electronically variable adjustable delays 116 and 118 are not limited to these types of delays. Any broadband DC-coupled electronically adjustable variable delay may be used.

As described in more detail below, the skew between the first input signal and the second input signal can be determined and then corrected by using the electronically variable adjustable delays 116 and 118. However, rather than using two variable adjustable delays 116 and 118 as shown in FIGS. 1-4, one input path may have an electronically variable adjustable delay, while the other input path has a fixed delay. In such embodiments, the electronically variable adjustable delay is adjusted to eliminate the skew.

Figure 5:
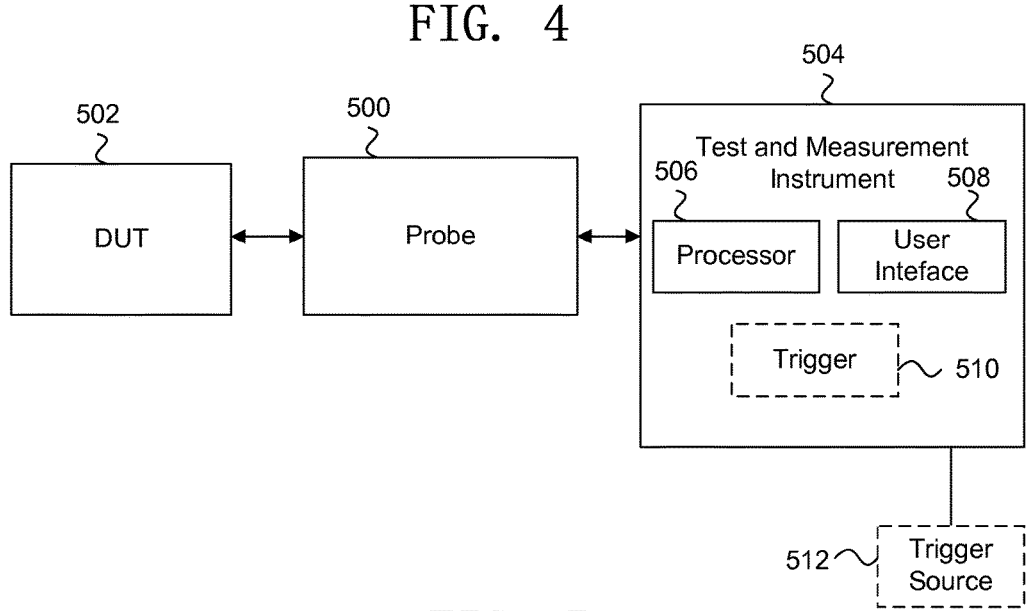
FIGS. 5 and 6 illustrate test and measurement systems using one of the probes of FIGS. 1-4 according to some embodiments of the invention.

In use, as seen in FIG. 5, probe 500 is attached to a device under test 502. Probe 500 may be any of the probes described above. Probe 500 is also connected to a test and measurement instrument 504. The test and measurement instrument 504 includes a processor 506 and a user interface 508, as described in more detail below. As also described in more detail below, the test and measurement instrument 504 may also include a trigger 510.

The probe 500 receives a differential signal from the device under test 502. Then, in some embodiments, the signals are sent to the processor 506 of the test and measurement instrument 504. The processor 506 can determine the skew amount for a differential signal from the device under test 502, and determine the amount of skew between the two sides of the differential signal. Once the skew is determined, the processor 506 sends instructions to the electronically variable adjustable delays 116 and 118 to adjust the delay amount of each side of the differential signal to eliminate or mitigate the amount of skew.

The processor 506 is preferably a digital processor, and the received signals or relevant parameters thereof are digitized before being sent to the processor. However, processor 506 may also be implemented as an analog processor designed to monitor the relevant parameters of the analog signals received, and control the electronically variable adjustable delays as further described below.

Figure 6:
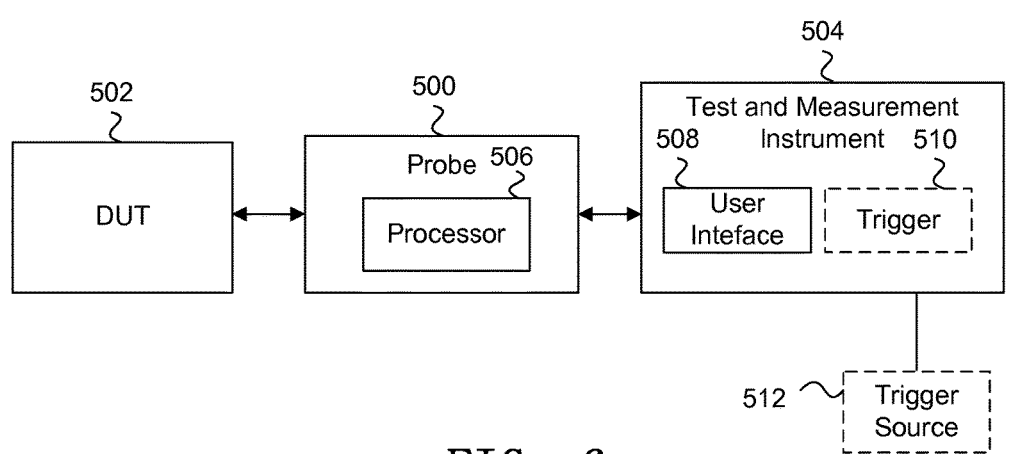

In various other embodiments, the processor 506 may be located within the probe 500 to determine the amount of skew, as shown in FIG. 6. The test and measurement instrument 504 or the probe 500 may also include a memory (not shown) for storing executable instructions for implementing the methods and processes described herein and for otherwise controlling the test and measurement instrument and/or the probe. Further, in other embodiments, the below described methods may be performed using a processor 506 in both the test and measurement instrument and the probe 500.

There are multiple methods possible to determine the amount of skew between the two sides of the differential signal via the processor 506. However, in each method, a reference signal with a defined timing relationship must be used as a standard against which to compare the differential signal. The method for determining the amount of delay to deskew the differential signal may be implemented in hardware, software, firmware, or any combination thereof.

Figure 7:
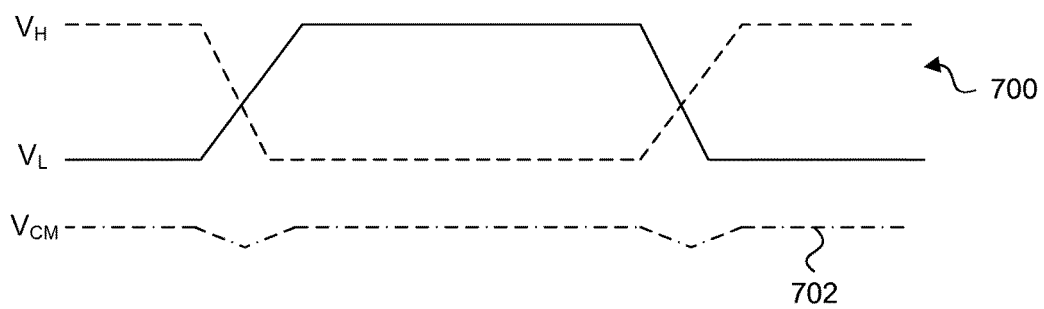
FIGS. 7 and 8 illustrate various differential and common mode signals.

One such reference signal is an assumed symmetric, but only nominally differential signal from the device under test 502, as shown in FIG. 7. The differential signal 700 includes $V_H$ and $V_L$. The common mode signal 702 is also shown as $V_{CM}$.

If both waveforms $V_H$ and $V_L$ can be captured simultaneously, it is easy to measure the average delay from the edges on one signal to corresponding edges on the other, taking care to average both polarity edges. Once the skew is determined, the electronically variable adjustable delays 116 and 118 may be adjusted until the average skew is zero, which results in removing the skew. For example, in FIG. 8, the $V_L$ edges of the differential signal 700 can be directly measured as being delayed from the $V_H$ edges, and the average delay measurement would directly determine the delay setting required to deskew the probe.

If probe 500, however, is programmed to capture each side of the differential signal at different times, that is, first one side of the differential signal and then the other side of the differential signal, then a separate trigger source 512 may be used. The separate trigger source 512 can be used as a common timing reference between the two captured signals of the differential signal. That is, the timing of each side of the differential signal can be determined based on the timing of the trigger source 512 signal.

Figure 8:
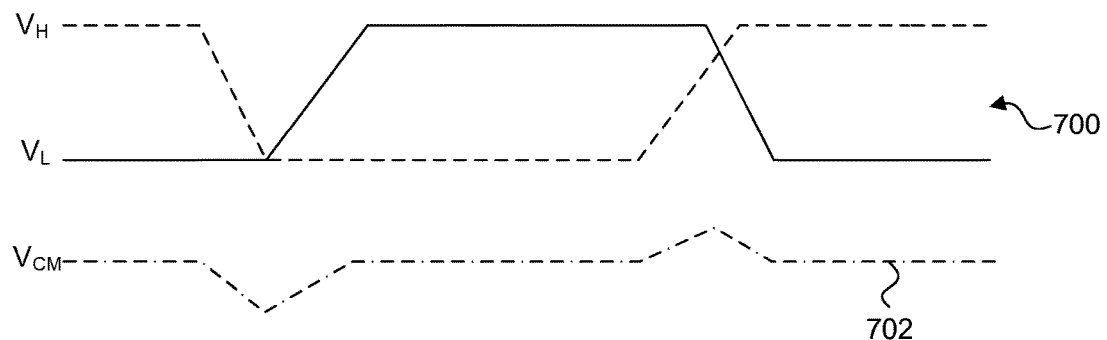

In other embodiments, the deskew amount can be determined by observing the common-mode signal rather than using a separate trigger source. A device under test 502 may produce some significant common-mode signal itself, for instance due to unequal rise and fall times, but if the device under test 502 is symmetric, the common-mode signal is the same for either polarity edge of the differential signal, as seen in FIG. 7. Mode conversion due to skew leads to a common-mode signal that depends on the edge polarity of the differential signal, as seen in FIG. 8. To automatically deskew the probe 500 observing this assumed-symmetric nominally differential signal, the probe 500 is programmed to observe the common-mode and the skew is adjusted to minimize the common-mode signal amplitude and/or to match the shape from one edge to the next. Knowledge of the baud rate of a high-speed serial signal may also help in identifying the locations of the common-mode shapes to be matched.

The differential signal can also be analyzed in the frequency domain to identify errors due to skew. For example, the common-mode signal due to skew in a nominally differential high-speed serial signal, such as shown in FIGS. 7 and 8, will have the highest frequency content at half the baud rate. The common-mode signal due to typical driver errors, e.g., unequal rise and fall times, will have the highest content at the baud rate.

The above discussed various methods to be performed by the processor 506 for removing skew will remove any skew from the point of the assumed-symmetric source onwards. Therefore, this compensates for skew in the user's channel if the device under test 502 is probed at the receiver end. If the user wants to remove skew due to the probe 500 but not skew due to the channel, a reference must be provided at the location of the probe 500. This can be done by shorting the two wires of the differential pair, ensuring the same signal on both wires and inputs 102 and 104 of the probe 500. Then, a probe 500 programmed to observe the differential signal will see no signal at all. If there is a signal present in the presence of the short, the processor can determine the amount of delay needed for each of the electronically variable adjustable delays 116 and 118, and set a delay amount that minimizes or eliminates the observed differential signal in the presence of the short.

The processor may also determine the amount to delay the electronically adjustable variable delays 116 and 118 based on observing the rise and fall times of a differential signal, and adjusting the electronically variable delays 116 and 118 to minimize the differential rise and fall times. In other embodiments, the processor can determine the amount to delay the electronically variable adjustable delays 116 and 118 by maximizing the energy in the frequency bands near half-integer multiples of the baud rate.

The test and measurement instrument 504 may also include a user interface 514. The user interface 514 allows a user to select having the probe 500 automatically determine the skew amount between the differential signals and correct it, or allowing a user to enter the amount of delay desired. Then the electronically variable adjustable delays 116 and 118 are adjusted based on the amount of delay entered by the user on the user interface 514.

Although the above described methods discuss adjusting the delay in electronically variable adjustable delays 116 and 118, as mentioned above, only one of the delays may be an electronically variable adjustable delay and the other may be a fixed delay. The electronically variable adjustable delay is adjusted while the fixed delay remains steady. That is, rather than providing an adjustment for both delays, one delay may be adjusted in relation to an input path with a fixed delay.

The above discussed methods for determining the amount of delay to deskew the differential signal can be implemented in hardware, software, firmware, or any combination thereof.

The term "processor" as used herein is intended to include microprocessors, microcomputers, ASICs, and dedicated hardware controllers, whether analog or digital, and associated memories. One or more aspects of the invention may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a non-transitory computer readable medium such as a hard disk, optical disk, removable storage media, solid state memory, RAM, etc. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects of the invention, and such data structures are contemplated within the scope of computer executable instructions and computer-usable data described herein.

Having described and illustrated the principles of the disclosed technology in a preferred embodiment thereof, it should be apparent that the disclosed technology can be modified in arrangement and detail without departing from such principles. We claim all modifications and variations coming within the spirit and scope of the following claims.

What is claimed is:

1. A probe comprising:
   a first input configured to receive a first input signal, the first input signal being a first of a pair of input signals forming a differential signal from a device under test;
   a second input configured to receive a second input signal, the second input signal being a second of the pair of input signals forming the differential signal from the device under test;
   a broadband electronically adjustable delay DC-coupled to the first input, the electronically adjustable delay configured to delay the first input signal to remove a skew between the first input signal and the second input signal;
   an amplifier configured to receive the first input signal from the electronically adjustable delay and the second input signal;
   an output configured to provide an output signal to a single input channel of a test and measurement instrument; and
   a processor connected to the broadband electronically adjustable delay, the processor configured to determine a delay adjustment amount by using a reference signal with a defined timing relationship as a standard against which to compare the differential signal.

2. The probe of claim 1, wherein the electronically adjustable delay is a first broadband electronically adjustable delay, and the probe further comprises a second broadband electronically adjustable delay DC-coupled to the second input, the second broadband electronically adjustable delay configured to delay the second input to remove the skew between the first input signal and the second input signal in combination with the first electronically adjustable delay.

3. The probe of claim 1, wherein the probe is a differential probe.

4. The probe of claim 1, wherein the probe is a TriMode probe, and the probe further includes a third input configured to receive a ground signal.

5. The probe of claim 1, wherein the broadband electronically adjustable delay is integrated within the amplifier.

6. A system for adjusting a skew between two input signals, comprising:
   the probe of claim 1; and
   a test and measurement instrument, distinct from but coupled to the probe, the test and measurement instrument including a processor configured to determine a delay adjustment amount for the broadband electronically adjustable delay.

7. The system of claim 6, wherein the test and measurement instrument further includes a user interface configured to accept entry of a delay adjustment amount for the broadband electronically adjustable delay from a user.

8. A method for correcting skew in a test and measurement probe between a first input signal and a second input signal, the method comprising:

receiving the first input signal, the first input signal being a first of a pair of input signals forming a differential signal from a device under test;

receiving the second input signal, the second input signal being a second of the pair of input signals forming the differential signal from the device under test;

determining an amount of skew between the first input signal and the second input signal by using a reference signal with a defined timing relationship as a standard against which to compare the differential signal; and adjusting a delay of at least one broadband DC-coupled electronically variable adjustable delay based on the amount of skew between the first input signal and the second input signal to remove the skew between the first input signal and the second input signal.

9. The method of claim 8, wherein determining the amount of skew between the first input signal and the second input signal includes measuring a first delay from a rising edge of the first input signal to a corresponding rising edge on the second input signal, measuring a second delay from a falling edge of the first input signal to a corresponding falling edge on the second input signal, and averaging the first and second delays.

10. The method of claim 8, further comprising receiving a trigger signal, wherein determining the amount of skew between the first input signal and the second input signal includes determining a common timing between the first input signal and the second input signal and measuring a delay from an edge of the first input signal to a corresponding edge of the second input signal based on the common timing.

11. The method of claim 8, wherein determining the amount of skew between the first input signal and the second input signal includes determining the amount of skew based on an amplitude of a common-mode signal.

12. The method of claim 8, wherein determining the amount of skew between the first input signal and the second input signal includes determining the amount of skew based on a frequency-domain analysis of a common-mode signal.

13. The method of claim 8, wherein determining the amount of skew between the first input signal and the second input signal includes determining the amount of skew based on an amplitude of a differential signal observed when the first input signal and second input signal are nominally matched except for skew.

14. The method of claim 8, wherein determining the amount of skew between the first input signal and the second input signal includes determining the amount of skew based on transition times of edges in a differential signal.

* * * * *